(12) United States Patent
Lazic

(10) Patent No.: US 9,386,987 B2
(45) Date of Patent: Jul. 12, 2016

(54) ANEURYSM CLIP

(71) Applicant: Peter Lazic GmbH, Tuttlingen (DE)

(72) Inventor: Daniel Lazic, Tuttlingen (DE)

(73) Assignee: Peter Lazic GmbH, Tuttlingen (DE)

(*) Notice: Subject to any disclaimer, the term of this patent is extended or adjusted under 35 U.S.C. 154(b) by 163 days.

(21) Appl. No.: 14/109,942

(22) Filed: Dec. 17, 2013

(65) Prior Publication Data

US 2014/0194908 A1   Jul. 10, 2014

(30) Foreign Application Priority Data

Jan. 8, 2013 (DE) .................. 10 2013 200 127

(51) Int. Cl.
*A61B 17/08* (2006.01)
*A61B 17/122* (2006.01)

(52) U.S. Cl.
CPC ........... *A61B 17/083* (2013.01); *A61B 17/1227* (2013.01)

(58) Field of Classification Search
CPC .. A61B 17/08; A61B 17/128; A61B 17/1227; A61B 17/083; A61B 17/122

USPC .......................................... 606/122, 151, 207
See application file for complete search history.

(56) References Cited

U.S. PATENT DOCUMENTS

2002/0111643 A1* 8/2002 Herrmann .......... A61B 17/1227
606/158
2010/0298849 A1* 11/2010 Lazic ................. A61B 17/1227
606/158

FOREIGN PATENT DOCUMENTS

| DE | 3523031 A1 | 1/1986 |
|---|---|---|
| DE | 203 03 496 U1 | 7/2003 |
| DE | 10309491 A1 | 9/2004 |
| DE | 10 2004 016 859 A2 | 10/2005 |
| DE | 10 2009 003 273 A1 | 11/2010 |

* cited by examiner

*Primary Examiner* — Victor Nguyen
(74) *Attorney, Agent, or Firm* — Hackler Daghighian & Martino

(57) ABSTRACT

A surgical clip, in particular an aneurysm clip, includes two rotatably connected clip parts, each having a clamping arm, an operating arm, and an interposed annular section with an opening. A leg spring pretensions the two clip parts into an initial rotation position. The pivot bearing of the two clip parts is formed by a bearing sleeve and the winding body of the leg spring is arranged at least in part inside the bearing sleeve.

5 Claims, 8 Drawing Sheets

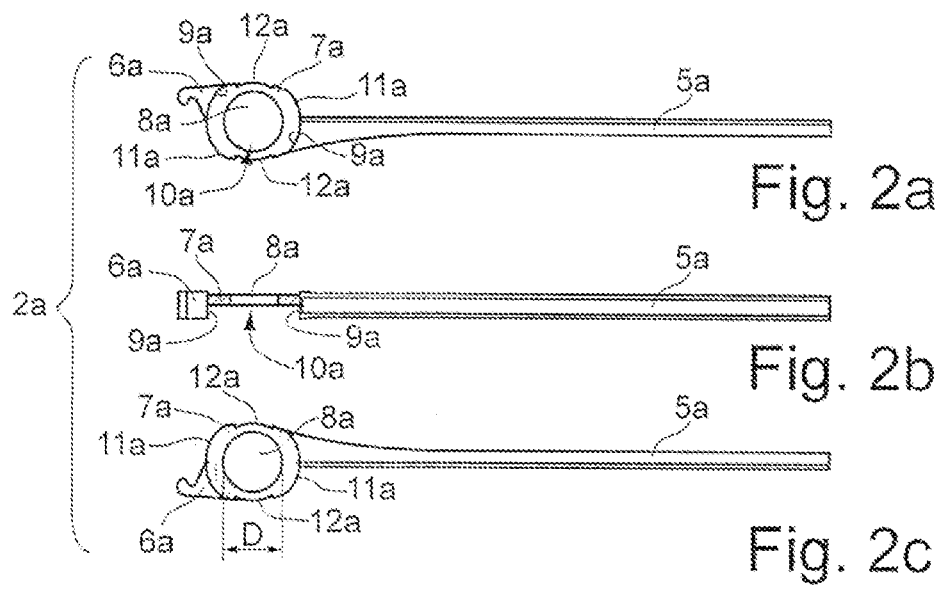
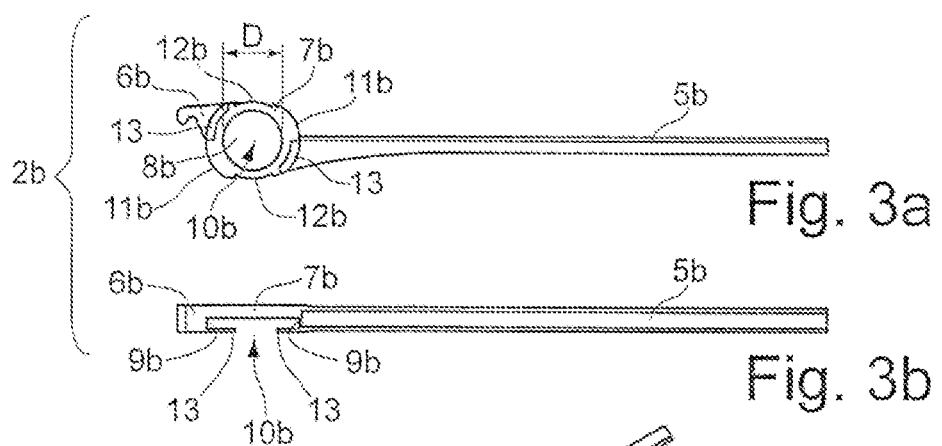
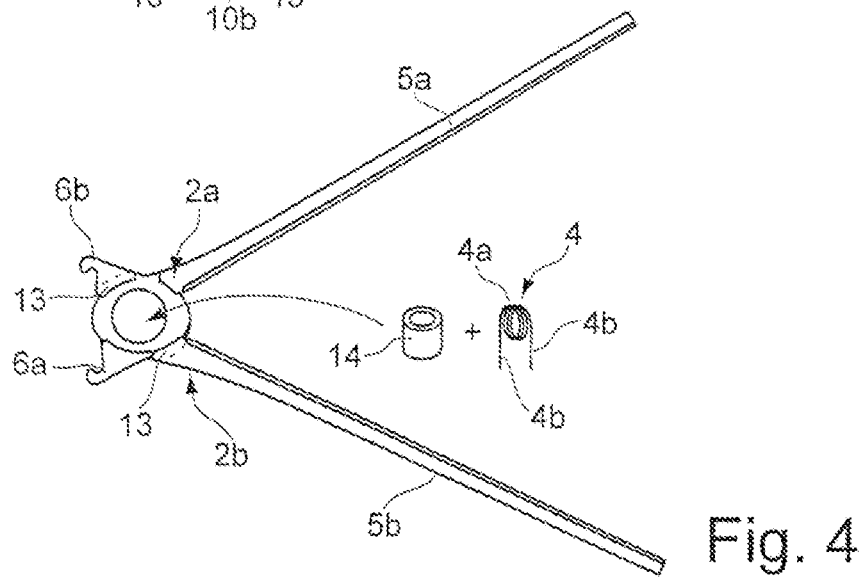

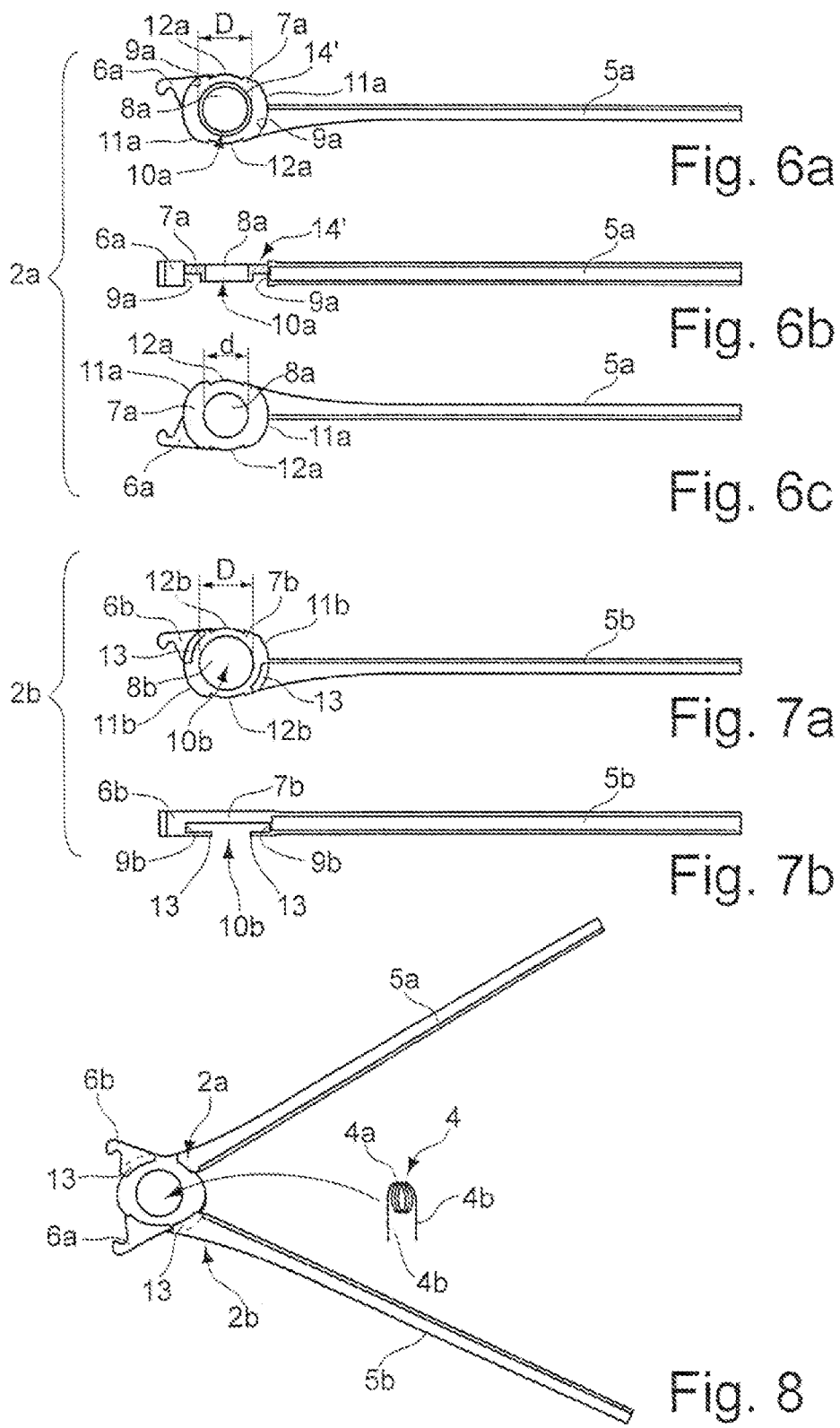

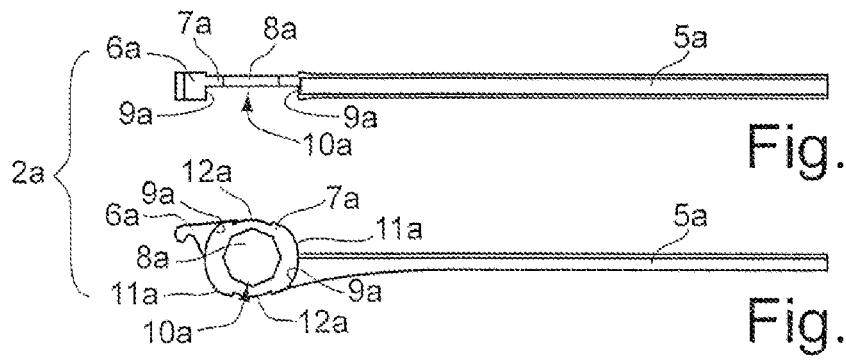
Fig. 10a
Fig. 10b
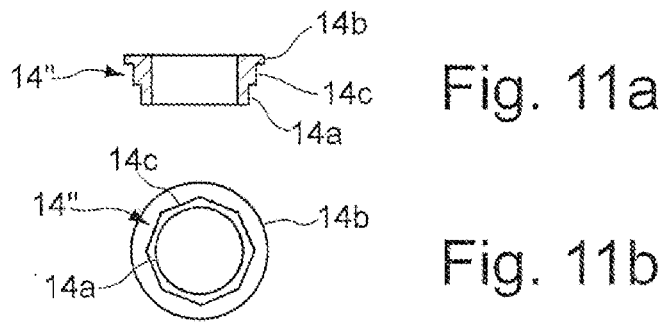
Fig. 11a
Fig. 11b
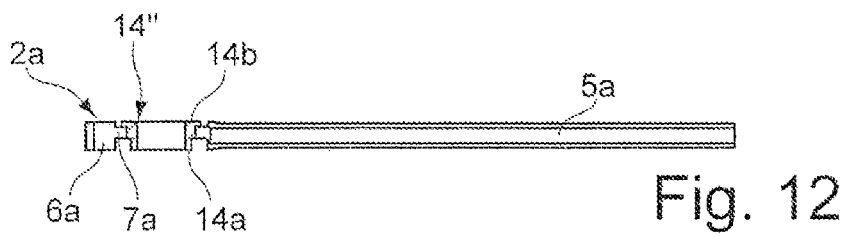
Fig. 12
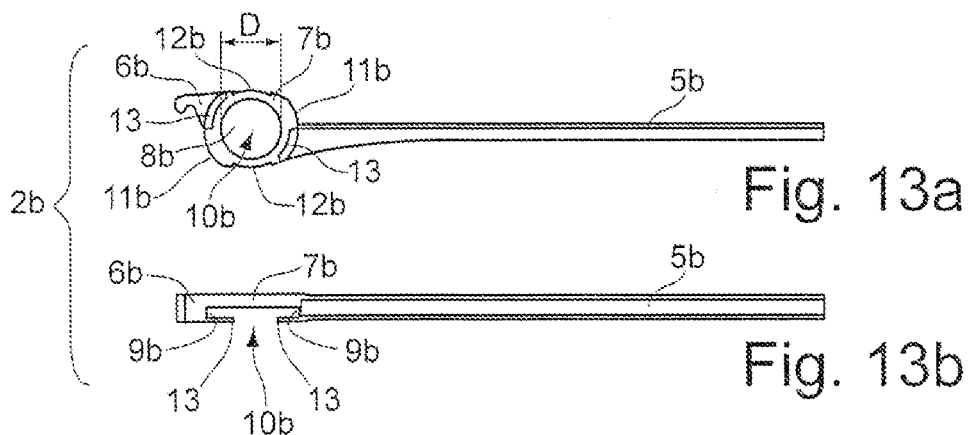
Fig. 13a
Fig. 13b

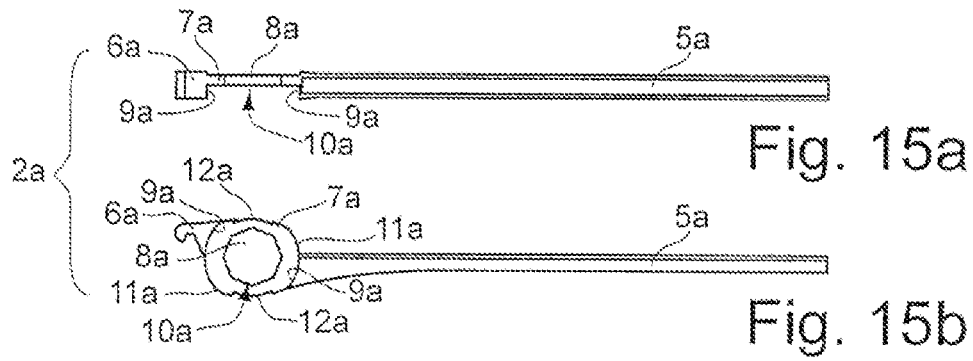
Fig. 15a
Fig. 15b
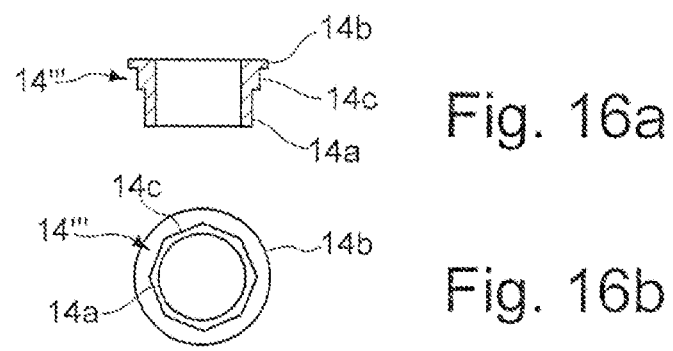
Fig. 16a
Fig. 16b
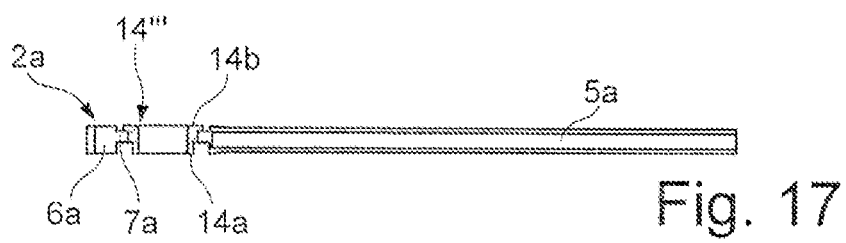
Fig. 17
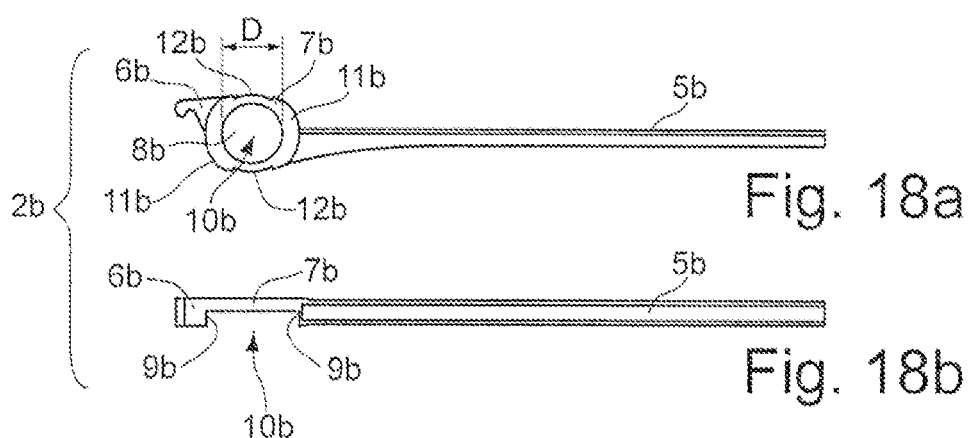
Fig. 18a
Fig. 18b

ANEURYSM CLIP

CROSS-REFERENCE TO RELATED APPLICATIONS

This application claims priority to German Patent Application No. 10 2013 200 127.4, filed Jan. 8, 2013, the entire contents of which are hereby incorporated by reference.

FIELD OF THE INVENTION

The invention relates to a surgical clip, such as an aneurysm clip, having two rotatably connected clip parts, each having a clamping arm, an operating arm, and an interposed annular section with an opening, and having a leg spring which pretensions the two clip parts into an initial rotation position.

BACKGROUND OF THE INVENTION

An aneurysm clip of this type is known e.g. from DE 10 2004 016 859 A1 or DE 10 2009 003 273 A1.

The aneurysm clip known from DE 10 2004 016 859 A1 comprises two rotatably connected clip parts, one of which, the first clip part, is fitted into a rotary receptacle of the other, second clip part and secured therein by a small guiding plate. Each rotary receptacle of the two clip parts has two pivot bearing sections which are disposed opposite to each other with respect to the axis of rotation and in which the respective other clip part is pivoted. However, each pivot bearing section only extends over an angle range of approximately 75°. The small guiding plate is welded to the second clip part after fitting together the two clip parts, thereby preventing detachment of the two clip parts in a direction opposite to the fitting direction. However, welding of the small guiding plate requires complex assembly, during which the welded plate is subsequently machined in order to prevent formation of burrs. A leg spring is finally arranged in a central opening of the two clip parts, the spring legs of which are welded to the two clip parts.

The aneurysm clip known from DE 10 2009 003 273 A1 comprises two clip parts which are connected to each other via a push-fit rotary lock and are pivoted. Each of the two clip parts has two pivot bearing sections which are disposed opposite to each other with respect to the axis of rotation, and in which the respective other clip part is pivoted. However, each pivot bearing section only extends over an angle range of less than 30°. A leg spring is disposed in a central opening of the two clip parts, the spring legs of which are welded to the two clip parts.

In contrast thereto, it is the object of the present invention to reduce the production cost and assembly work for a surgical clip of the above-mentioned type and also to further improve the pivot bearing of the two clip parts.

SUMMARY OF THE INVENTION

This object is achieved in accordance with the invention in that the pivot bearing of the two clip parts is formed by a bearing sleeve and the winding body of the leg spring is arranged at least in part inside the bearing sleeve.

The bearing sleeve thus forms the pivot bearing about which the two clip parts rotate. The bearing sleeve can either be a separate part or be non-rotatably connected to the clip part via a push-fit fitting or be produced in one piece with the clip part. In the first two cases, the surgical clip consists of four individual parts (two clip parts, bearing sleeve and leg spring), in the latter case, however, only of three individual parts (two clip parts and leg spring).

When the two clip parts are formed from weldable material, e.g. of titanium, the two spring legs of the leg spring can be welded to the two clip parts or alternatively be welded to the bearing sleeve, which is non-rotatably mounted to one of the clip parts, and be welded to the other clip part.

When the two clip parts are formed from non-weldable material, such as e.g. plastic material, in particular of polymethyl methacrylate (PMMA) or of X-ray transparent polyether etherketone (PEEK), one of the spring legs of the leg spring can be welded to the bearing sleeve, which is non-rotatably mounted to the one clip part, and the other spring leg can engage the other clip part, i.e. for example grip around the outer side of the other clip part—similar to a peg.

In order to prevent tissue contusion between the individual helical windings of the leg spring, all helical windings, i.e. the whole winding body of the leg spring, is/are completely arranged inside the bearing sleeve.

In one particularly preferred embodiment of the invention, the two clip parts are connected to each other via a push-fit rotary lock, wherein the two clip parts are axially fitted into one another in an assembly rotation position and are axially locked to each other by subsequent rotation in the direction towards the initial rotation position. The push-fit rotary lock permits the two clip parts to be fitted into one another and be rotatably guided without additional components and without additional assembly work.

In an advantageous further development of this embodiment, the annular section of at least one of the two clip parts has two first annular segments disposed opposite to each other with respect to the opening, and a respectively interposed second annular segment which is radially set back towards the inside with respect to the first annular segments, and at least the other clip part has a push-fit receptacle which is formed by two side walls disposed opposite to each other with respect to the opening, the side walls being provided with circumferential grooves, wherein in the assembly rotation position, the two second annular segments of one of the clip parts are fitted into the push-fit receptacle between the side walls of the respective other clip part, and upon subsequent rotation, the first annular segments of that clip part engage the circumferential grooves of the other clip part, thereby locking the two clip parts to each other in a direction opposite to the fitting direction.

In a further preferred embodiment of the invention, the two clip parts are also axially held together by the bearing sleeve, one end of which has an annular shoulder and the other end of which has a rivet head that is bent to the outside.

Further advantages of the invention can be extracted from the description, the claims and the drawing. The features mentioned above and below may be used individually or collectively in arbitrary combination. The embodiments shown and described are not to be understood as exhaustive enumeration but have exemplary character for describing the invention.

BRIEF DESCRIPTION OF THE DRAWINGS

The accompanying drawings illustrate the invention. In such drawings:

FIGS. 1a-1c show a first embodiment of the inventive aneurysm clip which is stuck together from two clip parts and a bearing sleeve, in the closed state in a top view of the one clip side (FIG. 1a), in a sectional view (FIG. 1b) and in a top view of the other clip side (FIG. 1c) which is not visible in FIG. 1a;

FIGS. 2a-2c show the first clip part illustrated in FIG. 1 in a top view of the clip part inner side (FIG. 2a), in a sectional view (FIG. 2b) and a top view of the clip part outer side (FIG. 2c);

FIGS. 3a, 3b show the other, second clip part illustrated in FIG. 1 in a top view (FIG. 3a), and in a side view (FIG. 3b);

FIG. 4 shows the two clip parts which, in order to obtain a push-fit rotary lock, are stuck into one another in a maximally open assembly rotation position and are rotatably disposed via the bearing sleeve;

FIGS. 5a-5c show a second embodiment of the inventive aneurysm clip which is stuck from two clip parts, in the closed state in a top view (FIG. 5a) of the one clip side, in a sectional view (FIG. 5b), and in a top view of the other clip side (FIG. 5c) which is not visible in FIG. 5a;

FIGS. 6a-6c show the first clip part illustrated in FIG. 5, which is produced in one piece with a bearing sleeve, in a top view of the clip part inner side (FIG. 6a), in a sectional view (FIG. 6b), and in a top view of the clip part outer side (FIG. 6c);

FIGS. 7a, 7b show the other, second clip part of FIG. 5 in a top view of the clip part inner side (FIG. 7a), and in a side view (FIG. 7b);

FIG. 8 shows the two clip parts which, in order to obtain a push-fit rotary lock, are stuck into one another in a maximally open assembly rotation position and are rotatably disposed via the bearing sleeve;

FIGS. 10a, 10b show the first clip part illustrated in FIG. 9 in a sectional view (FIG. 10a), and in a top view of the clip part inner side (FIG. 10b);

FIGS. 11a, 11b show the bearing sleeve illustrated in FIG. 9 in a sectional view (FIG. 11a), and in a top view (FIG. 11b);

FIG. 12 shows the first clip part of FIG. 10 with the bearing sleeve which is non-rotatably stuck therein, in a sectional view;

FIGS. 13a, 13b show the other, second clip part illustrated in FIG. 9 in a top view of the clip part inner side (FIG. 13a), and in a sectional view (FIG. 13b);

FIGS. 15a, 15b show the first clip part illustrated in FIG. 14 in a sectional view (FIG. 15a), and in a top view of the clip part inner side (FIG. 15b);

FIGS. 16a, 16b show the bearing sleeve illustrated in FIG. 14 in a sectional view (FIG. 16a), and in a top view (FIG. 16b);

FIG. 17 shows the first clip part of FIG. 15 with the bearing sleeve which is non-rotatably stuck therein, in a sectional view; and FIGS. 18a, 18b show the other, second clip part illustrated in FIG. 14 in a top view of the clip part inner side (FIG. 18a), and in a side view (FIG. 18b).

DETAILED DESCRIPTION OF THE PREFERRED EMBODIMENTS

Figure 1A:
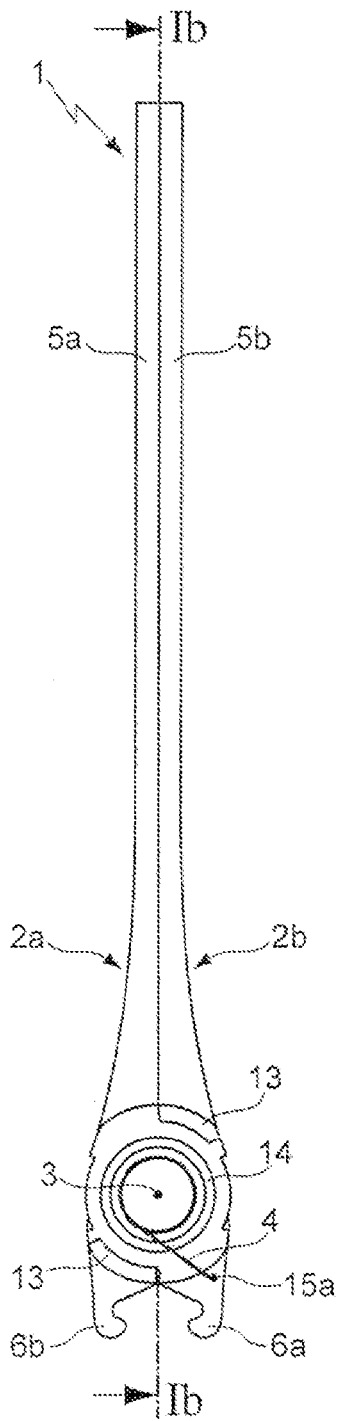

Identical components or components having the same function are designated by identical reference numerals in the following description of the drawing.

Figure 1B:
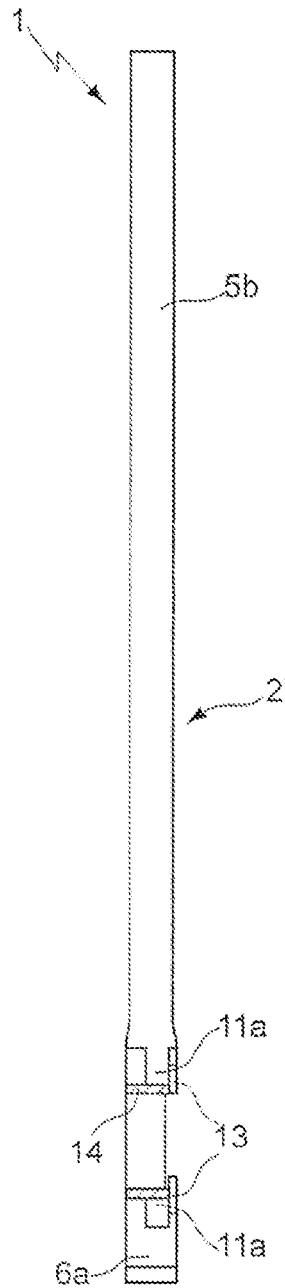
Figure 1C:
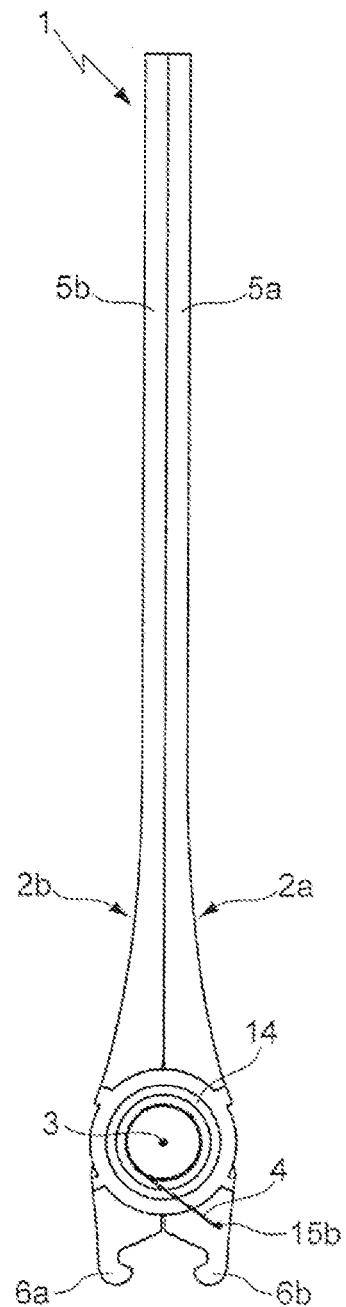

The aneurysm clip 1 shown in FIGS. 1a-1c comprises two two-armed clip parts 2a, 2b which are rotatably connected to each other about an axis of rotation 3 and are pretensioned into their closed end position by a leg spring 4 which comprises at least one winding.

Each of the two clip parts 2a, 2b has a long clamping arm 5a, 5b and a short operating arm 6a, 6b which are arranged opposite to each other with respect to the axis of rotation 3 and are displaced parallel with respect to each other. The operating arms 6a, 6b can be pushed apart against the closing force of the leg spring 4 by means of an applying forceps that grips between the two operating arms 6a, 6b, thereby opening the clamping arms 5a, 5b.

As is shown in FIGS. 2a-2c, the first clip part 2a has a flat annular section 7a with a circular opening 8a (opening diameter D) between the clamping arm 5a and the operating arm 6a. The annular section 7a is axially set back towards the inside with respect to the clamping and operating arms 5a, 6a by two steps 9a having the shape of a partial cylinder in order to thereby form a push-fit receptacle 10a that is open on the inside. The annular section 7a forms the bottom or the bottom plate of the push-fit receptacle 10a and the two steps 9a form two side walls of the push-fit receptacle 10a that are disposed opposite to each other with respect to the opening 8a. The annular section 7a has two first annular segments 11a which are disposed opposite to each other with respect to the opening 8a, and a respectively interposed second annular segment 12a, wherein the second annular segments 12a are each radially set back towards the inside with respect to the first annular segments 11a.

As is shown in FIGS. 3a, 3b, the other, second clip part 2b also has a flat annular section 7b with a circular opening 8b (opening diameter D) between the clamping arm 5b and the operating arm 6b. The annular section 7b is axially set back towards the inside with respect to the clamping and operating arms 5b, 6b by two steps 9b having the shape of a partial cylinder in order to thereby form a push-fit receptacle 10b that is open on the inside. The annular section 7b forms the bottom or the bottom plate of the push-fit receptacle 10b and the two steps 9b form two side walls of the push-fit receptacle 10b which are disposed opposite to each other with respect to the opening 8b. The annular section 7b has two first annular segments 11b which are disposed opposite to each other with respect to the opening 8b, and a respectively interposed second annular segment 12b, wherein the second annular segments 12b are each radially set back towards the inside with respect to the first annular segments 11b. The two steps 9b are each overlapped on the side opposite to the bottom plate 7b by a protrusion 13 and are thereby formed as circumferential grooves. The second clip part 2b can be formed identically to the first clip part 2a except for its two protrusions 13. The second ring segments 12 are not necessarily required, but allow the two clip parts 2a, 2b to be produced by the same unfinished parts.

For assembling the aneurysm clip 1, the second annular segments 12a of the first clip part 2a are oriented between the two protrusions 13 of the second clip part 2b and the second annular segments 12b of the second clip part 2b are oriented between the two steps 9a of the first clip part 2a and axially fitted into one another in this maximally open assembly rotation position shown in FIG. 4 until their flat bottom plates 7a, 7b abut each other on the inside and the openings 8a, 8b coincide. A bearing sleeve 14 is then fitted through these openings 8a, 8b, wherein the round outer diameter of the bearing sleeve 14 corresponds to the opening diameter D of the circular openings 8a, 8b except for a minimum bearing clearance. The bearing sleeve 14 therefore forms the pivot bearing about which the two clip parts 2a, 2b rotate. The length of the bearing sleeve 14 maximally corresponds to the overall thickness of the two annular sections 7a, 7b such that the bearing sleeve 14 is flush with the outer sides of the two clip parts 2a, 2b or is set back.

The two clip parts 2a, 2b are subsequently rotated towards their closed end position to form a push-fit rotary lock, as a result of which the first annular segments 11a of the first clip part 2a engage the circumferential grooves 9b of the second clip part 2b, thereby axially connecting the two clip parts 2a, 2b to each other or locking them in a direction opposite to the fitting direction.

The winding body 4a of the leg spring 4 is finally arranged in the bearing sleeve 14 and the two spring legs 4b of the leg spring are then welded to the outside of the operating arms 6a, 6b at 15a, 15b (FIG. 1). As a result, the two clip parts 2a, 2b are pretensioned into their closed initial rotation position and are secured in the assembly rotation position in a direction opposite to the fitting direction, and the bearing sleeve 14 is also undetachably held between the two legs 4b in the aneurysm clip 1. The length of the bearing sleeve 14 is advantageously smaller than the overall thickness of the two annular sections 7a, 7b in order to prevent any friction between the bearing sleeve 14 and the legs 4b.

Instead of being welded to the two clip parts 2a, 2b the two spring legs can alternatively grip around the outer side of the two operating arms 6a, 6b—similar to a peg. In this case, the two clip parts 2a, 2b can also be formed from non-weldable material such as e.g. plastic material, in particular of polymethyl methacrylate (PMMA) or of X-ray transparent polyether etherketone (PEEK).

Figure 5A:
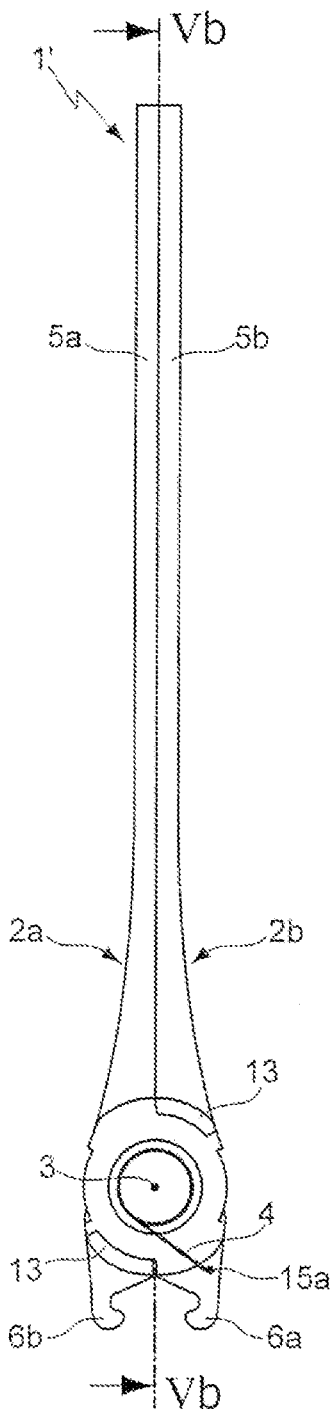
Figure 5B:
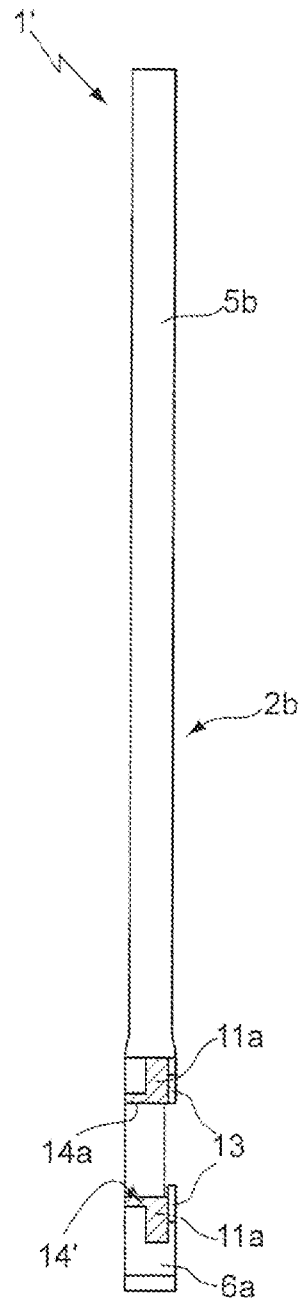
Figure 5C:
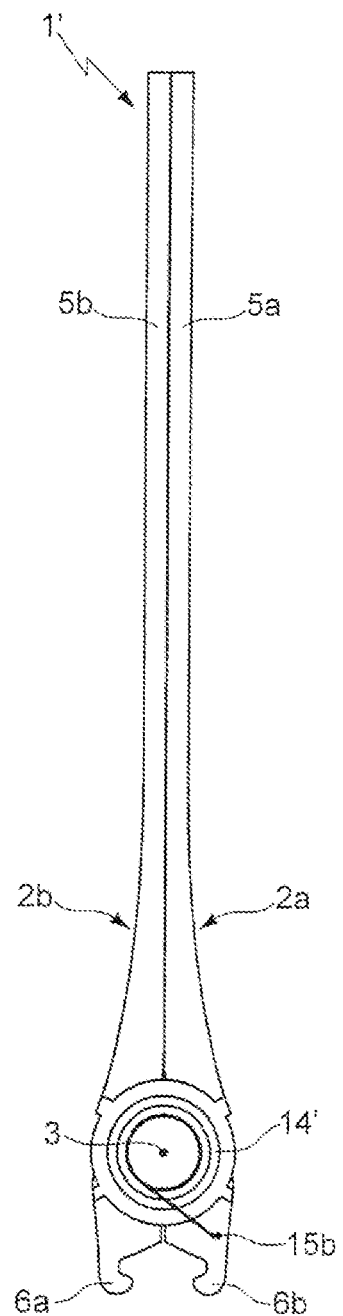

The aneurysm clip 1' shown in FIG. 5 differs from the aneurysm clip 1 of FIG. 1 only in that its bearing sleeve 14' is produced in one piece with the first clip part 2a. As is shown in FIGS. 6a-6c, the bearing sleeve 14' (outer diameter D) projects axially past the annular section 7a. The sleeve opening (inner diameter d) of the bearing sleeve 14' extends continuously to the outer side of the clip part, thereby defining the opening 8a of the annular section 7a. The second clip part 2b of the aneurysm clip 1' shown in FIGS. 7a, 7b is formed identically to the clip part 2b of FIGS. 3a, 3b.

For assembling the aneurysm clip 1', the second annular segments 12a of the first clip part 2a are oriented between the two protrusions 13 of the second clip part 2b and the second annular segments 12b of the second clip part 2b are oriented between the two steps 9a of the first clip part 2a and the two clip parts are axially fitted into one another in this maximally open assembly rotation position shown in FIG. 8 until the bearing sleeve 14' of the first clip part 2a has been fitted into the opening 8b of the second clip part 2b and the insides of the two flat bottom plates 7a, 7b abut each other. The bearing sleeve 14' thus forms the pivot bearing about which the two clip parts 2a, 2b rotate. The projecting length of the bearing sleeve 14' maximally corresponds to the thickness of the annular section 7b of the second clip part 2b such that the bearing sleeve 14' is flush with the outer side of the second clip part 2b or is axially set back. The length of the bearing sleeve 14' is advantageously smaller than the thickness of the annular section 7b in order to prevent any friction between the bearing sleeve 14' and the legs 4b.

The two clip parts 2a, 2b are subsequently rotated towards their closed end position in order to obtain a push-fit rotary lock, as a result of which the first annular segments 11a of the first clip part 2a engage in the circumferential grooves 9b of the second clip part 2b, thereby axially connecting the two clip parts 2a, 2b to each other or locking them in a direction opposite to the fitting direction.

The winding body 4a of the leg spring 4 is finally arranged in the sleeve opening 8a of the bearing sleeve 14' and the two legs 4b of the leg spring are subsequently welded to the outside of the operating arms 6a, 6b at 15a, 15b (FIG. 5). As a result, the two clip parts 2a, 2b are pretensioned into their closed initial rotation position and are secured in the assembly rotation position in a direction opposite to the fitting direction.

Figures 9A, 9B:
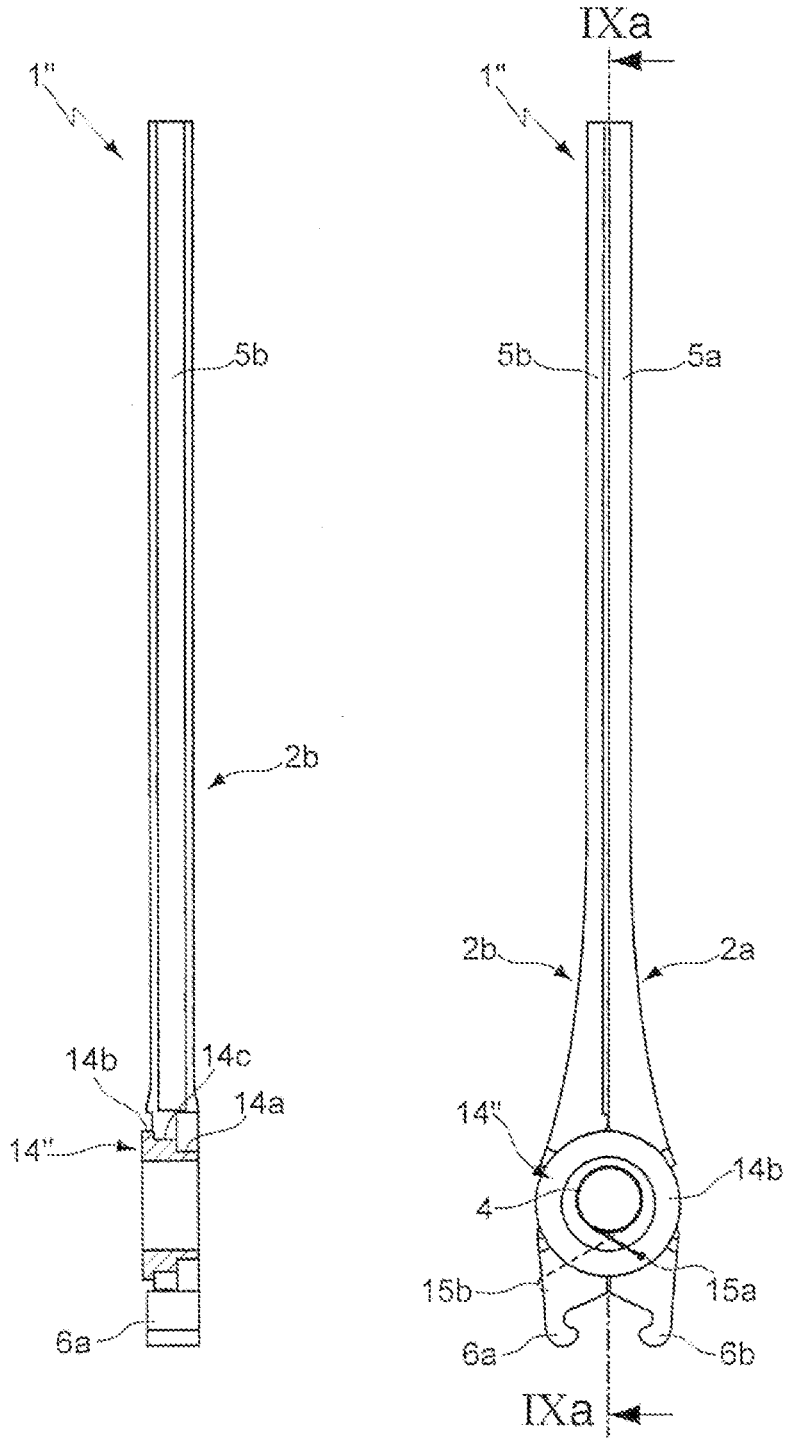
FIGS. 9a, 9b show a third embodiment of the inventive aneurysm clip which is stuck from two clip parts and a bearing sleeve, in the closed state in a sectional view (FIG. 9a), and in a top view (FIG. 9b)

The aneurysm clip 1" shown in FIGS. 9a, 9b differs from the aneurysm clip 1 of FIG. 1 only in that its bearing sleeve 14" is non-rotatably fitted into the first clip part 2a. The first clip part 2a of the aneurysm clip 1" shown in FIGS. 10a, 10b has an opening 8a with an octagonal opening cross-section and the bearing sleeve 14" shown in FIGS. 11a, 11b has a bearing section 14a of circular outer cross-section at one end and at the other end an annular shoulder 14b as well as an interposed fitting section 14c of octagonal outer cross-section, wherein the fitting section 14c is radially set back towards the inside with respect to the annular shoulder 14b and the bearing section 14a is radially set back towards the inside with respect to the fitting section 14c. As is shown in FIG. 12, the octagonal fitting section 14c of the bearing sleeve 14" is fitted into the octagonal opening 8a of the first clip part 2a and thus held non-rotatably therein. The annular shoulder 14b of the bearing sleeve 14" abuts the outside of the annular section 7a of the first clip part 2a and its circular bearing section 14a projects towards the inside past the annular section 7a. The opening cross-section of the opening 8a and the outer cross-section of the fitting section 14c can have any other non-circular cross-section, e.g. another polygonal or an oval cross-section. The second clip part 2b of the aneurysm clip 1" shown in FIGS. 13a, 13b is formed identically to the clip part 2b of FIGS. 3a, 3b.

The first clip part 2a with fitted bearing sleeve 14" and the second clip part 2b are assembled like the aneurysm clip 1' shown in FIG. 5. The bearing sleeve 14" thus forms the pivot bearing about which the second clip part 2b rotates. The projecting length of the bearing section 14b of the bearing sleeve 14" maximally corresponds to the thickness of the annular section 7b of the second clip part 2b such that the bearing sleeve 14" is either flush with the outer side of the second clip part 2b or is axially set back. The winding body of the leg spring 4 is finally arranged in the sleeve opening of the bearing sleeve 14" and its two spring legs are then mounted to the two clip parts 2a, 2b in order to pretension the two clip parts 2a, 2b into the closed end position. In the shown embodiment, one spring leg of the leg spring 4 is welded to the bearing sleeve 14" at 15a, namely advantageously already prior to fitting the bearing sleeve 14" into the first clip part 2a, and its other spring leg grips around the operating arm 6b of the second clip part 2b at 15b—similar to a peg. The leg spring 4 is thus not welded to the clip parts 2a, 2b such that the clip parts 2a, 2b can also be produced from a non-weldable material such as e.g. plastic material, in particular of polymethyl methacrylate (PMMA) or of X-ray transparent polyether etherketone (PEEK). The length of the bearing section 14b is advantageously smaller than the thickness of the annular section 7b in order to prevent any friction between the bearing sleeve 14" and the legs 4b.

If the clip parts 2a, 2b are made from a weldable material, the leg spring 4 can be welded to the operating arm 6b of the second clip part 2b—as with the aneurysm clips 1, 1'—and can optionally also be welded to the operating arm 6a of the first clip part 2a instead of being welded to the bearing sleeve 4".

Figures 14A, 14B:
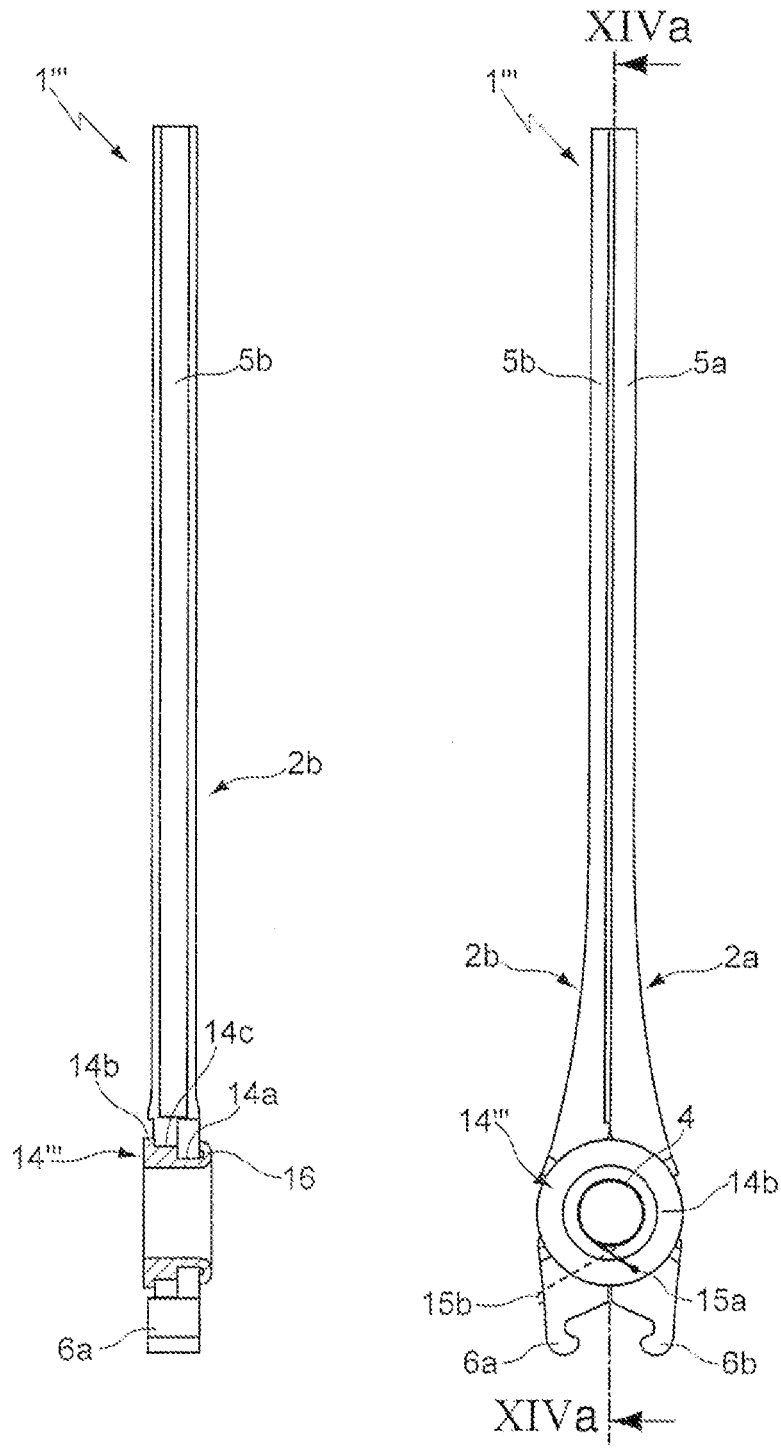
FIGS. 14a, 14b show a fourth embodiment of the inventive aneurysm clip which is stuck from two clip parts and a bearing sleeve, in the closed state in a sectional view (FIG. 14a), and in a top view (FIG. 14b)

The aneurysm clip 1'" shown in FIGS. 14a, 14b differs from the aneurysm clip 1" of FIG. 9 only in that the two clip parts 2a, 2b are connected to each other by bending the bearing sleeve 14'" and not through a push-fit rotary lock. The first clip part 2a of the aneurysm clip 1''' shown in FIGS. 15a, 15b is formed identically to the clip part 2a of FIGS. 10a, 10b. The bearing sleeve 14''' shown in FIGS. 16a, 16b differs from the bearing sleeve 14'' shown in FIG. 11 only in that it has a longer bearing section 14a. FIG. 17 shows the first clip part 2a with the bearing sleeve 14''' which has been fitted non-rotatably therein. The second clip part 2b of the aneurysm clip 1''' shown in FIGS. 18a, 18b is formed identically to the clip part 2b of FIGS. 3a, 3b except for the missing projections 13.

The first clip part 2a with fitted bearing sleeve 14''' and the second clip part 2b are assembled like the aneurysm clip 1'' shown in FIG. 9. The bearing sleeve 14''' thus forms the pivot bearing about which the second clip part 2b rotates. The end of the longer bearing section 14b of the bearing sleeve 14''' that projects past the outer side of the second clip part 2b is bent to the outside to form a rivet head 16 in order to attach the two clip parts 2a, 2b to each other or axially hold them together.

Although several embodiments have been described in detail for purposes of illustration, various modifications may be made to each without departing from the scope and spirit of the invention. Accordingly, the invention is not to be limited, except as by the appended claims.

What is claimed is:

1. A surgical clip comprising:
   two rotatably connected clip parts, each clip part having a clamping arm, an operating arm, and an interposed annular section with an opening;
   a pivot bearing formed by a bearing sleeve, the bearing sleeve being disposed at least partially inside the opening of the two rotatably connected clip parts; and
   a leg spring which pretensions the two clip parts into an initial rotation position and a winding body of which is arranged at least in part inside the bearing sleeve, wherein the bearing sleeve is non-rotatably mounted to a first clip part and has a bearing section which is fitted into the circular opening of a second clip part and is pivoted therein,
   wherein the bearing sleeve is a separate component and has a fitting section of non-circular outer cross-section which is non-rotatably fitted into the non-circular opening of the first clip part;
   wherein the two clip parts comprise non-weldable material; and
   wherein one spring leg of the leg spring is welded to the bearing sleeve and the other spring leg engages the second clip part.

2. The surgical clip according to claim 1, wherein the winding body of the leg spring is arranged completely inside the bearing sleeve.

3. The surgical clip according to claim 1, wherein the annular section of at least one of the two clip parts has two first annular segments which are disposed opposite to each other with respect to the opening, and a respectively interposed second annular segment which is radially set back towards the inside with respect to the first annular segments, and at least the other clip part has a push-fit receptacle which is formed by two side walls which are disposed opposite to each other with respect to the opening and are provided with circumferential grooves, wherein in an assembly rotation position, the two second annular segments of one of the clip parts are fitted into the push-fit receptacle between the side walls of the respective other clip part and through subsequent rotation, the first annular segments of the one clip part engage the circumferential grooves of the other clip part, thereby locking the two clip parts to each other in a direction opposite to the fitting direction.

4. The surgical clip according to claim 1, wherein the two clip parts are axially held together by the bearing sleeve, one end of which has an annular shoulder and the other end of which has a rivet head that is bent to the outside.

5. The surgical clip according to claim 1, wherein the flat inner surfaces of the annular sections of the two clip parts, which face each other, lie on top of each other.

* * * * *